Figure 1:
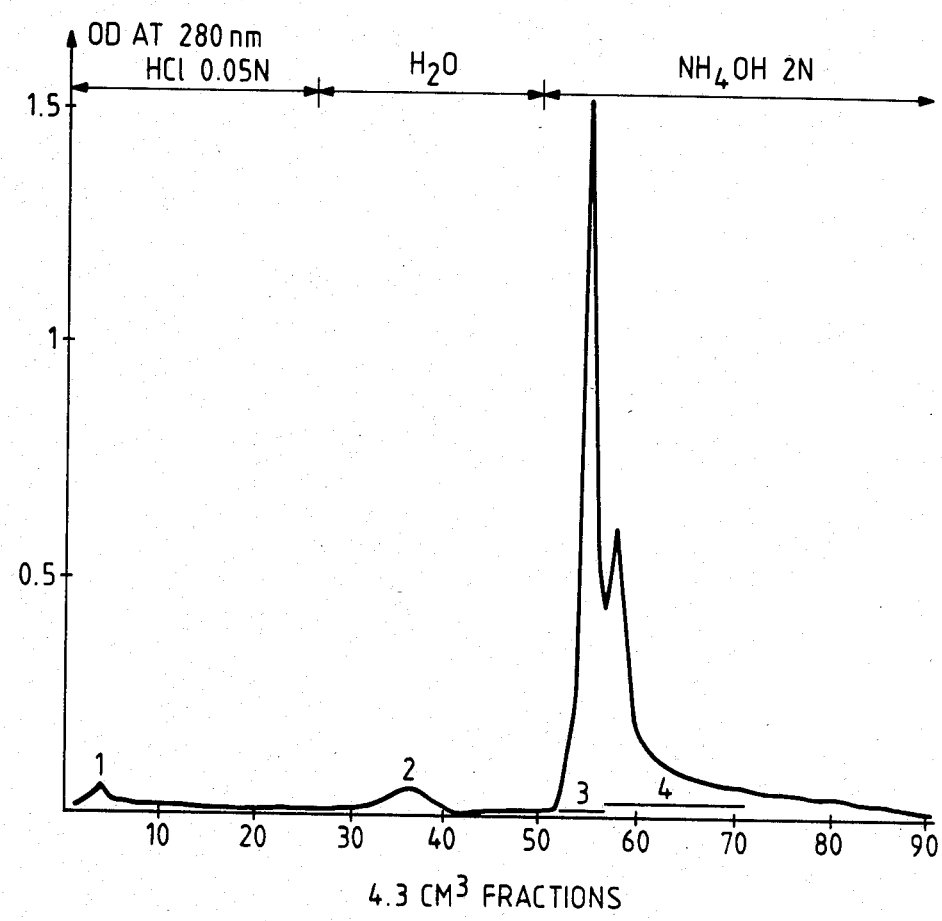

United States Patent [19]

Jolles et al.

[11] Patent Number: 4,637,997

[45] Date of Patent: Jan. 20, 1987

[54] HEXAPEPTIDE, PROCESS FOR OBTAINING II AND THE PHARMACEUTICAL COMPOSITIONS CONTAINING II

[75] Inventors: Pierre Jolles, Paris; Danièle Migliore-Samour, Le Kremlin-Bicétre; Fabienne Parker, St. Maur des Fosses, all of France; Monika Casaretto, Monchen-Gladbach, Fed. Rep. of Germany

[73] Assignee: Institut National de la Sante et de la Recherche Medicale, Paris, France

[21] Appl. No.: 697,903

[22] Filed: Feb. 4, 1985

[30] Foreign Application Priority Data

Feb. 7, 1984 [FR] France .................... 84 01816

[51] Int. Cl.$^4$ ..................... A61K 37/43; C07K 7/06
[52] U.S. Cl. ................................. 514/17; 530/329
[58] Field of Search .................. 260/112.5 R; 514/17; 530/329

[56] References Cited

U.S. PATENT DOCUMENTS 3,558,770 1/1971 Gordon et al. .............. 260/112.5 R
4,462,990 7/1984 Jolles et al. .................. 260/112.5 R

FOREIGN PATENT DOCUMENTS 0049666 4/1982 European Pat. Off. .

OTHER PUBLICATIONS

Parker et al., *Eur. J. Biochem.*, 145(3), 677–682 (1984).

*Primary Examiner*—Delbert R. Phillips
*Attorney, Agent, or Firm*—Stevens, Davis, Miller & Mosher

[57] ABSTRACT

The hexapeptide of formula

Val-Glu-Pro-Ile-Pro-Tyr        (I)

which can be isolated from the hydrolysis products of human casein or synthesized from the amino acid residues which it contains, has immunological properties.

3 Claims, 3 Drawing Figures

HEXAPEPTIDE, PROCESS FOR OBTAINING IT AND THE PHARMACEUTICAL COMPOSITIONS CONTAINING IT

This invention relates to hexapeptides of therapeutic interest, to their preparation and to compositions containing them.

European Specification No. 49 666, published Apr. 14th 1982 and corresponding to U.S. Pat. No. 4,462,990, the contents of which is herein incorporated by reference, describes substances designated MJH-24, MJH-63 and MJH-65 and their preparation from delipidised human casein which has been treated with trypsin.

MJH-24, MJH-63 and MJH-65, which are purified substances, have remarkable properties. They are immunological agents which promote the production of antibodies and which accelerate the phenomenon of phagocytosis.

It has now been found, and this is the subject of the present invention, that fractionation and purification of the substance MJH-63 under specific conditions make it possible to isolate a new hexapeptide which possesses the immunological properties of MJH-63 in a higher degree.

The new hexapeptide has the formula:

Val-Glu-Pro-Ile-Pro-Tyr    (I)

In formula (I), Val denotes L-valine, Glu denotes L-glutamic acid, Pro denotes L-proline, Ile denotes L-isoleucine and Tyr denotes L-tyrosine.

To obtain the hexapeptide of formula (I), the following sequence of operations may be carried out on MJH-63 in aqueous solution:
(a) filtration on an ultra-filtration membrane, preferably a Diaflo-Amicon UM-05 membrane, to remove most of the sodium chloride;
(b) filtration on a Sephadex G-15 column, followed by chromatography on a Dowex 50-X-4 column, to remove completely the sodium chloride and the Tris buffer;
(c) purification by high performance liquid chromatography (HPLC).

Each filtration and purification step is under determined conditions and is followed by measurement of the absorption at 220 and 280 nm of the fractions collected.

The composition and the structure of the hexapeptide of formula (I) has been determined:
 by total hydrolysis with 6N hydrochloric acid at 110° C. for 18 hours;
 by dansylation, to determine the nature of the N-terminal amino acid; and
 by automatic degradation with a Beckmann model 890 C sequencer.

The hexapeptide of formula (I) may also be synthesised chemically by application of the methods known in peptide chemistry.

For example, the hexapeptide of formula (I) may be prepared by application of the methods for chain lengthening by condensation of appropriate, suitably protected amino acids or peptides, followed by the removal of the protective groups. More particularly, the hexapeptide of formula I may be made by reacting the dipeptide of formula Boc-Val-Glu(OBu$^t$)-OH with the tetrapeptide of formula H-Pro-Ile-Pro-Tyr-OMe, to obtain the hexapeptide of formula Boc-Val-Glu(OBu$^t$)-Pro-Ile-Pro-Tyr-OMe, and removing the protective groups to obtain the hexapeptide.

In more detail, the dipeptide of formula:

Z-Pro-Tyr-OMe    (II)

in which Z denotes a protective group for the amino function, preferably the t-butyloxycarbonyl (Boc) group, after removal of the protective group Z, may be condensed successively with isoleucine and proline whose amino function has previously been protected, to give the tetrapeptide of formula:

H-Pro-Ile-Pro-Tyr-OMe    (III)

which is then condensed with the dipeptide of formula:

Z-Val-Glu(Z$_1$)-OH    (IV)

in which Z is defined as above and Z$_1$ denotes a protective group for the acid function, preferably the t-butyloxy (OBu$^t$) group, to give the hexapeptide of formula:

Z-Val-Glu(Z$_1$)-Pro-Ile-Pro-Tyr-OMe    (V)

from which the protective groups for the acid functions may be removed by saponification in the presence of nargase derived from *Bacillus subtilis*, and from which the protective group for the amino function may be removed, for example, by means of trifluoroacetic acid in an organic solvent such as anisole, to give the hexapeptide of formula (I).

The dipeptide of formula (II) may be obtained by condensation of Z-Pro with Tyr-OMe.

The dipeptide of formula (IV) may be obtained by condensation of Z-Val with Glu(Z$_1$)-OH.

The condensation of the amino acids or peptides whose amino functions are suitably protected may be carried out in the presence of a condensing agent such as dicyclohexylcarbodiimide or by employing a mixed anhydride of the amino acid or of the peptide obtained, for example, with an alkyl haloformate or N-hydroxysuccinimide (ONSu).

The hexapeptide of formula (I) thus obtained may be purified by chromatography on a suitable support. It is particularly advantageous to carry out chromatography on an ion exchange column.

The hexapeptide of formula (I) obtained by chemical synthesis has the same properties as the product obtained by purification of the natural product.

The hexapeptide of formula (I) is an immunological agent which promotes the production of antibodies and which accelerates the phenomenon of phagocytosis.

In vitro, it has been found particularly active at concentrations of between 0.1 and 10 ug/cm$^3$ in the test for secretion of sheep anti-red cell (haemolytic) antibodies by mouse spleen cells immunised in vivo and in the test for phagocytosis of sheep opsonised red cells by mouse peritoneal macrophages.

In vivo, the hexapeptide of formula (I) exhibits, in the mouse, a remarkable activity starting at a dose of 0.05 mg/kg i.v. against experimental infection with *Klebsiella pneumoniae*.

The following Examples illustrate the preparation of the hexapeptide according to the invention.

EXAMPLE 1

The product MJH-63, the preparation of which is described in Example 3 of the aforesaid European Patent No. 49,666, is filtered on a Diaflo-Amicon UM-05 membrane, and is then filtered on a column of Sephadex G-15 (height 120 cm; diameter 1.2 cm), with elution with 10% acetic acid at an elution rate of 9 cm$^3$/hour and with 0.6 cm$^3$ fractions being collected.

The fractions eluted between 72 and 84 cm$^3$ are combined and then chromatographed on a column of Dowex 50-X-4 (height 14 cm; diameter 1.4 cm), 4.3 cm$^3$ fractions being collected. The elution is carried out at a rate of 24 cm$^3$/hour, the following eluents being employed in succession:
(1) 0.05N hydrochloric acid (100 cm$^3$)
(2) water (100 cm$^3$)
(3) 2N aqueous ammonia The elution diagram is shown in the accompanying FIG. 1. The fractions which correspond to the elution between 12 and 36 cm$^3$ of 2N aqueous ammonia are combined (fraction 3, MJH-72).

Continuation of the elution with the same solvent yields a second active fraction (fraction 4, MJH-73).

Fraction 3, MJH-72, is purified by "reverse" phase HPLC on a semi-preparative column (C$_{18}$-μ-bondapack column, WATERS) the length of which is 30 cm and the diameter 7.8 mm. 0.5 cm$^3$ fractions are collected, the rate of elution being 1 cm$^3$/minute. At the outset, the column is buffered with 0.1% phosphoric acid (eluent A). An eluent containing phosphoric acid (0.1% by volume) and acetonitrile (70% by volume) in water (eluent B) is prepared. Fraction 3, MJH-72, is dissolved in 250 μl of 0.1% phosphoric acid.

The elution is carried out by employing a linear elution gradient and by proceeding according to the following table:

| Time (minutes) | Eluent A | Eluent B |
| --- | --- | --- |
| 0 | 100 | 0 |
| 10 | 100 | 0 |
| 110 | 50 | 50 |
| 140 | 0 | 100 |

Figure 2:
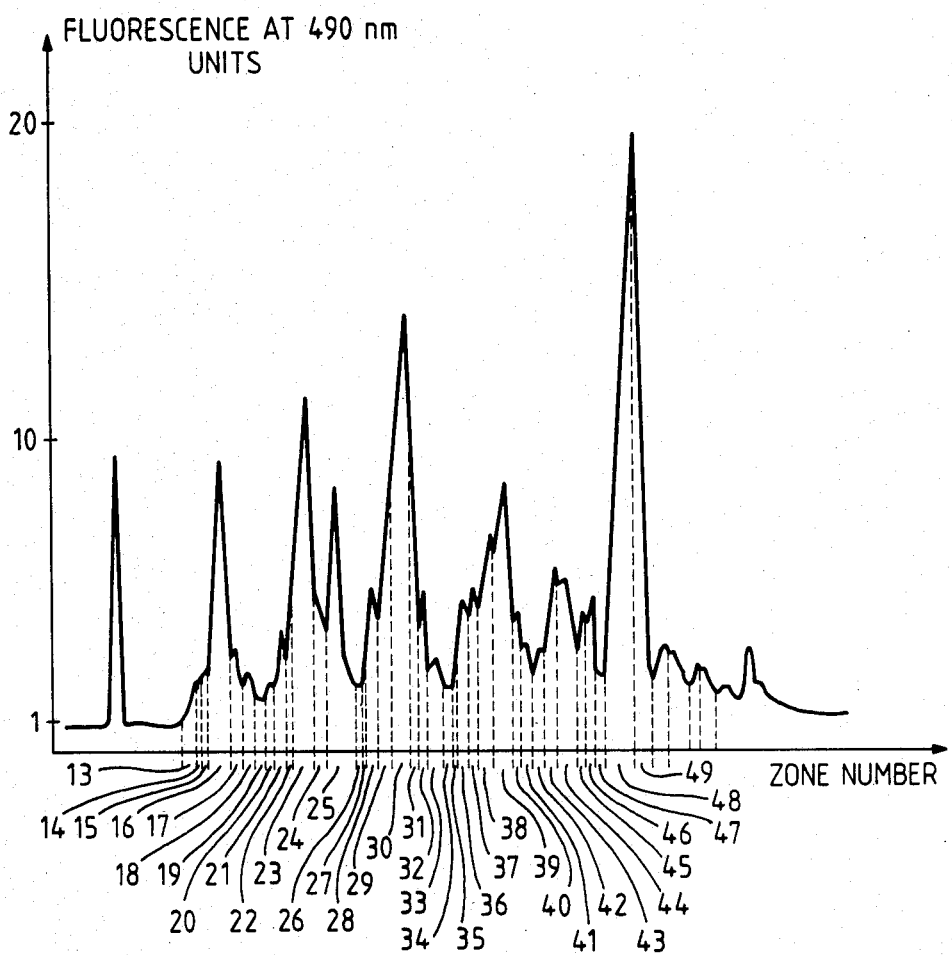

The elution diagram is shown in FIG. 2. The elution is followed by measuring the absorption at 280 nm and at 220 nm, and by reading at 490 nm the fluorescence after reaction with fluorescamine.

The elution diagram contains 49 zones, the most important of which in respect of biological activity are zones 41 to 47 (MJH-153) and zone 49 (MJH-155). Their retention times are respectively 80 to 89 minutes and 91 to 93 minutes.

Fraction 49 (MJH-155) is purified again by HPLC on a column of the same type as that employed earlier, the length of which is 30 cm and the diameter 3.9 mm. 0.5 cm$^3$ fractions are collected, the rate of elution being 1 cm$^3$/minute. The following eluents are prepared:
  eluent A: 0.1% trifluoroacetic acid
  eluent B: trifluoroacetic acid (0.1% by volume) and acetonitrile (70% by volume) in water.
The elution is carried out by employing a linear elution gradient and by proceeding according to the following table:

| Time (minutes) | Eluent A | Eluent B |
| --- | --- | --- |
| 0 | 80 | 20 |
| 15 | 80 | 20 |
| 30 | 70 | 30 |

Figure 3:
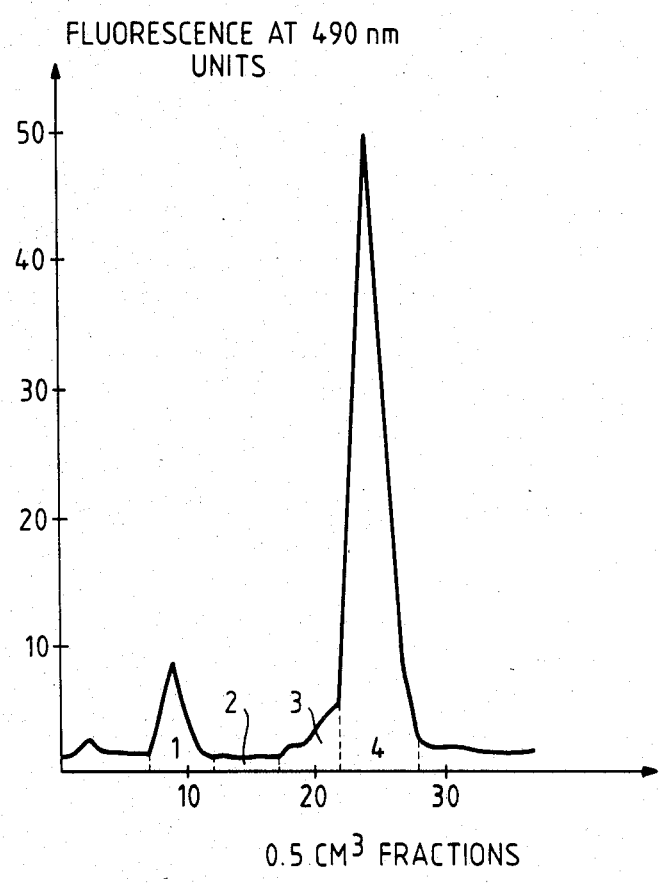

The elution diagram is shown in FIG. 3.

The elution diagram contains 4 peaks, Peak No. 4, eluted between 11.5 minutes and 13.5 minutes, corresponding to the fraction containing the pure hexapeptide of formula (I).

The structure of the hexapeptide is determined:
- by total hydrolysis with 6N hydrochloric acid at 110° C. for 18 hours, which shows the presence of glutamic acid (Glu)=1, proline (Pro)=2, valine (Val)=1, isoleucine (Ile)=1 and tyrosine (Tyr)=1
- by dansylation, in order to determine the nature of the N-terminal amino acid, which is valine
- by analysis using the Beckmann Model 890 C sequencer Quadrol 0.1 M program, with determination of the various steps by virtue of characterisation of the phenylthiohydantoin-amino acids (determination by HPLC and development on plates).

EXAMPLE 2

In the following, the purity of the products is determined by thin layer chromatography with the use of the following solvent systems:
  chloroform-methanol-acetic acid (95-5-5 by volume): R$_f$1
  2-butanol-formic acid (90%)-water (75-13.5-11.5 by volume): R$_f$2
  methanol-ethyl acetate-water (30-80-5 by volume): R$_f$3
  n-butanol-acetic acid-pyridine-water (15-3-10-12 by volume): R$_f$4.

Analysis of the amino acids is carried out after hydrolysis in 6N hydrochloric acid at 110° C. for 24 hours.

The synthesis of the hexapeptide is carried out in the following manner:

(1) 6.45 g of Boc-Pro (30 mmol) are dissolved in 20 cm$^3$ of dimethylformamide. After cooling to −15° C. neutralisation is carried out by addition of 3.3 cm$^3$ of N-methylmorpholine (30 mmol) and then 3.93 cm$^3$ of isobutyl chloroformate (30 mmol) are added.

After 2 minutes, a solution of 6.95 g of Tyr-OMe hydrochloride (30 mmol) and 3.3 cm$^3$ of N-methylmorpholine (30 mmol) in 10 cm$^3$ of dimethylformamide is added. The reaction mixture is stirred for 1 hour at −15° C. and for 2 hours at 20° C. The solvent is evaporated off under reduced pressure. The residue obtained is dissolved in ethyl acetate and the solution obtained is washed successively with a 1M solution of citric acid, a solution of sodium bicarbonate and a solution of sodium chloride.

The organic layer is dried over sodium sulphate. After removal of the solvent under reduced pressure, the oil obtained is taken up several times with ethyl ether to give 11.3 g of Boc-Pro-Tyr-OMe in the form of an amorphous foam, the properties of which are as follows:
  melting point 57°–59° C.
  $[\alpha]_D^{22} = -34.2°$ (c=1, methanol)
  R$_f$1=0.96; R$_f$3=0.95
  The yield is 96%.

(2) 6.4 g of Boc-Pro-Tyr-OMe are treated with 10 cm$^3$ of a solution of trifluoroacetic acid in anisole for 30 minutes at 20° C. The acid is removed under reduced pressure. The residue is dissolved in dimethylformamide and the solution is neutralised by adding 1.8 cm$^3$ of N-methylmorpholine (16 mmol).

A solution of 3.5 g of Boc-Ile (16 mmol) is reacted with 3.8 g of 1-hydroxybenzotriazole (2.4 mmol) and 3.7 g of N,N'-dicyclohexylcarbodiimide (18 mmol) for 1 hour at 0° C., and then the solution of Pro-Tyr-OMe in 15 cm$^3$ of dimethylformamide, prepared earlier, is added. After stirring for 1 hour at 0° C. and then for 10 hours at 20° C., the precipitate of dicyclohexylurea is separated off by filtration and the filtrate is concentrated. The residue obtained is dissolved in ethyl acetate and the solution obtained is washed successively with a 1M solution of citric acid, a solution of sodium bicarbonate and a solution of sodium chloride. The organic layer is dried over sodium sulphate. After removal of the solvent, the crude product is purified by chromatography on a column of silica gel (height 45 cm, diameter 2.5 cm), by eluting with ethyl acetate and mixtures of ethyl acetate with hexane. 3.8 g of Boc-Ile-Pro-Tyr-OMe are obtained, the properties of which are as follows:

melting point: 68° C.
$[\alpha]_D^{22} = -55.9°$ (c=1, methanol)
$R_f 1 = 0.85$; $R_f 3 = 0.91$
analysis for amino acids: Ile 1.00 (1), Pro 1.00 (1), Tyr 0.95 (1).
The yield is 50.1%.

(3) 2.4 g of Boc-Ile-Pro-Tyr-OMe (4.8 mmol) are treated with a solution of trifluoroacetic acid in anisole in the usual manner. The acid is removed under reduced pressure. The residue is dissolved in dimethylformamide and the solution obtained is neutralised by adding 0.55 cm$^3$ of N-methylmorpholine (4.8 mmol).

1.05 g of Boc-Pro (4.8 mmol) are dissolved in 10 cm$^3$ of tetrahydrofuran cooled to $-15°$ C. 0.55 cm$^3$ of N-methylmorpholine (4.8 mmol) is then added, followed by 0.64 cm$^3$ of isobutyl chloroformate (4.8 mmol). After 2 minutes, the solution of Ile-Pro-Tyr-OMe in 5 cm$^3$ of dimethylformamide which was prepared earlier is added. After stirring for 1 hour at $-15°$ C. and for 2 hours at 20° C., the reaction mixture is treated in the usual manner. The 2.6 g of crude product obtained in this way are purified by chromatography on silica gel by eluting with a mixture of ethyl acetate with petroleum ether (1-1 by volume) and then by a mixture of ethyl acetate with methanol (95-5 by volume) and lastly by a new chromatography by eluting with a mixture of ethyl acetate and methanol (98-2 by volume). In this way 1.9 g of Boc-Pro-Ile-Pro-Tyr-OMe are obtained, the properties of which are as follows:

melting point: 70°-71° C.
$[\alpha]_D^{22} = -100.4°$ (c=1, methanol)
$R_f 1 = 0.9$; $R_f 2 = 0.84$
analysis for amino acids after 48 hours' hydrolysis: Pro 1.99 (2), Ile 1.00 (1), Tyr 0.99 (1).
The yield is 65.7%.

(4) 4.5 g of Boc-Val-ONSu (15 mmol) (ONSu=N-hydroxysuccinimide) are added to a solution of 3.65 g of H-Glu-(OBu$^t$)-OH (18 mmol) and 3.0 g of sodium bicarbonate (36 mmol) in 40 cm$^3$ of a mixture of dioxane and water (2-1 by volume). The reaction mixture is stirred for 2 hours at 20° C. The dioxane is removed under reduced pressure. The residue is extracted with ethyl acetate. The organic phase is washed with a 1M solution of citric acid and with water. The purification is completed by 160-pass countercurrent extraction with a mixture of n-butanol and water. 4.8 g of Boc-Val-Glu(OBu$^t$)-OH are thus obtained in the form of an oil. The yield is 79.5%.

(5) 1.0 g of Boc-Pro-Ile-Pro-Tyr-OMe (1.66 mmol) is treated with a solution of trifluoroacetic acid in anisole in the usual manner. Neutralisation is carried out by adding 0.19 cm$^3$ of N-methylmorpholine.

0.8 g of Boc-Val-Glu(OBu$^t$)-OH (1.9 mmol) is dissolved in 5 cm$^3$ of tetrahydrofuran cooled to $-15°$ C. 0.21 cm$^3$ of N-methylmorpholine (1.9 mmol) and 0.25 cm$^3$ of isobutyl chloroformate are added in succession. After 2 minutes, the solution of Pro-Ile-Pro-Tyr-OMe in 5 cm$^3$ of dimethylformamide, prepared earlier, is added. The reaction mixture is stirred for 1 hour at $-15°$ C. and then for 2 hours at 20° C. The solvents are removed under reduced pressure. The 1.2 g of crude product obtained are purified by chromatography on silica gel by eluting with mixtures of ethyl acetate and petroleum ether (1-1; 7-2 and 8-2 by volume). The main fraction is purified by chromatography on silica gel by eluting with methylene chloride containing 3% of methanol (by volume). In this way, 0.6 g of Boc-Val-Glu(OBu$^t$)-Pro-Ile-Pro-Tyr-OMe is obtained, the properties of which are as follows:

melting point: 100°-102° C.
$[\alpha]_D^{22} = -101.9°$ (c=1, methanol)
$R_f 1 = 0.92$; $R_f 4 = 0.4$
analysis for amino acids: Val 1.00 (1); Glu 1.02 (1), Pro 1.84 (2), Ile 0.93 (1), Tyr 1.00 (1).
The yield is 40.7%.

(6) The saponification of 100 mg of Boc-Val-Glu(OBu$^t$)-Pro-Ile-Pro-Tyr-OMe (1.1 mmol) dissolved in 10 cm$^3$ of dioxane/0.1N as sodium acetate (pH=7.5) is catalysed with 1 mg of nargase derived from *Bacillus subtilis*. After 3 hours, the reaction mixture is extracted with ether. The aqueous phase is acidified to pH 3 and then extracted with ethyl acetate. 70.1 mg of crude product are thus obtained, and treated for 30 minutes with 5 cm$^3$ of a solution of trifluoroacetic acid in anisole. The acid is removed under reduced pressure and the residue is triturated in ethyl ether, dissolved in 10% acetic acid and then desalinated by filtration on Sephadex G 25.

The lyophylisate is purified by ion exchange chromatography on a column of DEAE Sephadex A 25 by eluting with a gradient of 0.1–0.5M ammonium bicarbonate.

In this way, 48.3 mg of H-Val-Glu-Pro-Ile-Pro-Tyr-OH are obtained, the properties of which are as follows:
$R_f 4 = 0.66$
analysis for amino aoids: Val 1.04 (1), Glu 1.00 (1), Ile 0.96 (1), Pro 1.87 (2), Tyr 0.97 (1)
protein content: 98.2%
racemisation test: Glu 2.44%; Tyr 1.2%; Ile 1.41%; Val 1%.

The present invention also provides pharmaceutical compositions which can be employed in human or veterinary therapy, which contain the hexapeptide according to the present invention in combination with one or more compatible and pharmaceutically acceptable diluents or adjuvants. Such compositions are useful for stimulating the immune systems of a host animal.

These compositions may be employed as adjuvants for vaccines (for example anti-flu vaccine consisting of haemagglutinant subunits, antipoliomyelitis vaccine containing inactivated virus, or anti-malaria vaccine) as a simultaneous injection with the antigen (viral, bacterial, parasitic, fungal) in respect of which it is desired to increase the production of antibodies or the specific cell reactivity.

The new pharmaceutical compositions may also be employed as non-specific immunoslimulants with a view to increasing the resistance of the host (human or domestic animal) to infections.

As an adjuvant, the product may be administered in aqueous solution, or in oil-based emulsion, or in the form of liposomes with the antigen in respect of which it is desired to produce an increased or improved immune response, by the route employed for this antigen and in proportions ranging between 0.01 and 10 times the quantity of antigen with which they are mixed before being injected.

For application as a non-specific immunostimulant, the hexapeptide of formula (I) may be administered by an intravenous, intramuscular, subcutaneous, intranasal, or, if appropriate, oral or rectal route, as an aqueous solution, or oil-based emulsion, or in the form of liposomes.

In this case the dosage of hexapeptide according to the invention is generally between 0.01 and 25 mg/kg. In human therapy, the daily dosage depends on the effect which is sought. It can be between 0.1 and 10 mg for an adult.

Solid compositions for oral administration may be tablets, pills, powders or granules.

As liquid compositions for oral administration, use can be made of pharmaceutically acceptable emulsions, solutions, suspensions, syrups or elixirs.

Compositions for parenteral or intranasal administration may be sterile aqueous solutions, suspensions or emulsions.

Sterilisation may be carried out in various ways, for example with the aid of a bacteriological filter, or by addition of sterilising agents. Solid compositions sterilised by irradiation ($\beta$ rays) may be dissolved in sterile water or any other injectable sterile medium, at the time of use if necessary.

Compositions for rectal administration are suppositories.

The following Example illustrates a composition according to the present invention.

EXAMPLE

A liquid composition which can be administered by intravenous route, with the following composition, is prepared according to the usual method:
hexapeptide of formula (I): 50 mg
injectable solution: 5 cm$^3$

We claim:
1. The hexapeptide of formula

Val-Glu-Pro-Ile-Pro-Tyr in which the amino acids are in L form.

2. A pharmaceutical composition, comprising the hexapeptide of formula

Val-Glu-Pro-Ile-Pro-Tyr in which the amino acids are in L form, as claimed in claim 1 in combination with one or more compatible and pharmaceutically acceptable diluents or adjuvants.

3. Method of stimulating the immune system of a host animal, which comprises administering thereto an effective amount of the hexapeptide of claim 1.

* * * * *